United States Patent [19]

McNaughton et al.

[11] Patent Number: 5,339,825

[45] Date of Patent: Aug. 23, 1994

[54] APPARATUS TO MEASURE AND RECORD PEAK AIR PASSAGE PRESSURE

[75] Inventors: John McNaughton; Derek P. Hutchison, both of Harlow, England

[73] Assignee: Clement Clarke International Ltd., Essex, England

[21] Appl. No.: 868,707

[22] Filed: Apr. 15, 1992

[30] Foreign Application Priority Data

Apr. 18, 1991 [GB] United Kingdom ............... 9108370.9

[51] Int. Cl.$^5$ ............................................. A61B 5/08
[52] U.S. Cl. ................................... 128/725; 128/716; 128/719
[58] Field of Search ......... 128/716, 719, 720, 725–728

[56] References Cited

U.S. PATENT DOCUMENTS

| | | | |
|---|---|---|---|
| 2,538,785 | 1/1951 | Karig . | |
| 3,958,565 | 5/1976 | Wright . | |
| 3,977,394 | 8/1976 | Jones et al. | 128/728 |
| 3,991,304 | 11/1976 | Hillsman | 128/720 |
| 4,241,739 | 12/1980 | Elson | 128/725 |
| 4,444,201 | 4/1984 | Itoh | 128/716 |
| 4,558,710 | 12/1985 | Eichler . | |
| 4,807,641 | 2/1989 | Beohringer et al. | 128/725 |
| 5,058,601 | 10/1991 | Riker . | |

FOREIGN PATENT DOCUMENTS

| | | | |
|---|---|---|---|
| 8912423 | 12/1989 | PCT Int'l Appl. | 128/725 |
| 2238389 | 5/1991 | United Kingdom | 128/725 |

*Primary Examiner*—Stephen C. Pellegrino
*Assistant Examiner*—M. Peffley
*Attorney, Agent, or Firm*—Burns, Doane, Swecker & Mathis

[57] ABSTRACT

The apparatus measure the exhalation of a subject and stores selected data relating to the peak value of the air pressure during exhalation. The storing unit for the data stores the peak values for a plurality of time periods and the apparatus can collect a series of measurements over an extended time period. Auxiliary information and data relating to each measurement can also be stored in the storing unit. A dedicated power source may be incorporated for holding the stored information in the storing unit.

10 Claims, 2 Drawing Sheets

APPARATUS TO MEASURE AND RECORD PEAK AIR PASSAGE PRESSURE

FIELD OF THE INVENTION

This invention relates to apparatus for the measurement of air pressures and/or flows and the like, in particular for medical testing of lung function.

BACKGROUND OF THE INVENTION

Apparatus is already known for measuring the peak flow rate of exhalation, in which the subject blows into a measurement container to move a piston in the container against the force of a spring, the displacement of the piston progressively uncovering an open slot in the container wall through which the subject's exhalation escapes. The rate of exhalation determines the movement of the piston and the maximum displacement of the piston is thus related to the peak exhalation flow. In British Patent Application No. 2238130 such an apparatus is described in which data processing means are provided for the pressure values measured, and the disclosure of that earlier application is incorporated herein by reference.

Peak flow meters have been used for many years by medical staff to measure lung function. More recently, therapeutic techniques have involved the subjects themselves in measuring their lung function and this has given rise to problems not encountered during clinical use. It is not always easy to ensure that a subject has properly recorded the results he has achieved using the apparatus, and some subjects may use the apparatus in ways that gives false results.

SUMMARY OF THE INVENTION

According to the present invention, there is provided a respiratory test apparatus comprising pressure sensing means for producing signals of air pressure during the exhalation of a subject, means for processing the signal data to derive a peak value for the pressure produced during an exhalation, and means for selecting and storing a plurality of highest values of peak pressure from a succession of exhalations within a predetermined time period, and means for reading the stored values.

With such an apparatus, when the subject is required to record the best of a series of tests it is possible to eliminate any subjective selection of the measured results and the apparatus can be used without the need to exercise skill or judgement. Means may be provided, however, for the subject to input manually additional information to be stored with the test data, e.g. that exercise has been undertaken or medication administered preceding the tests.

The apparatus is preferably designed for a lengthy period of use between consultations with the subject's physician and it can be provided with a data store capable of holding a series of groups of the best of three readings. For example, the store may require the capacity to record the results from three sets of tests each day for at least 30 days. Conveniently, a dedicated power source is provided in the apparatus for the purpose of operating a clock of the data processing means and to hold the accumulated readings in store.

For use on successive occasions, the clock associated with the data processing system can also be read at the times of the tests, so that it can be checked that they have been properly spaced over the period between successive consultations. It is possible to provide the apparatus with means for indicating the times at which a test is due, including a visual or audible alarm to alert the subject.

BRIEF DESCRIPTION OF THE DRAWINGS

By way of example, the invention will be described in more detail with reference to the accompanying drawings, in which.

DETAILED DESCRIPTION OF THE PREFERRED EMBODIMENT

Figure 1:
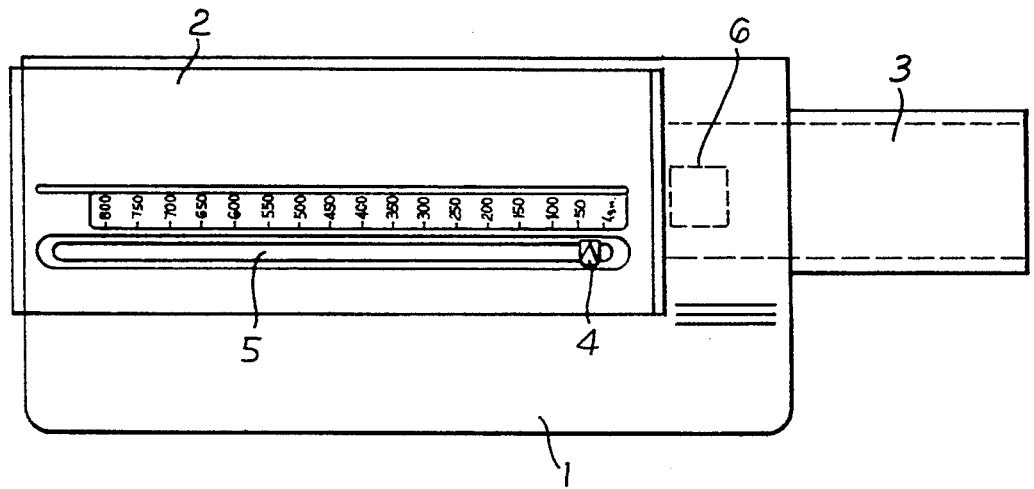
FIG. 1 shows a top view of the respiratory test apparatus according to the present invention.

As shown in FIG. 1, the external form and the manner in which a pressure reading is generated in the apparatus of the present invention can be similar to the apparatus disclosed in our earlier British patent application No. 2238130 and the disclosure therein is incorporated herewith by reference. The apparatus shown in FIG. 1 has a casing 1 and a cylinder 2 mounted in the casing 1. A removable mouth piece 3 is connected to the cylinder 2 thus a subject can blow air into the apparatus through the mouth piece 3. The air pressure in the apparatus displaces a spring-loaded piston (not shown) along the cylinder 2, the piston having a pointer 4 secured to it and visible in an axial slot 5 in the cylinder 2 against a scale. The movement of the piston represents the static pressure rise in the cylinder against its spring loading. The pressure also acts as a pressure transducer 6 in a manner which is described in more detail in earlier British Application 2238130.

Figure 2:
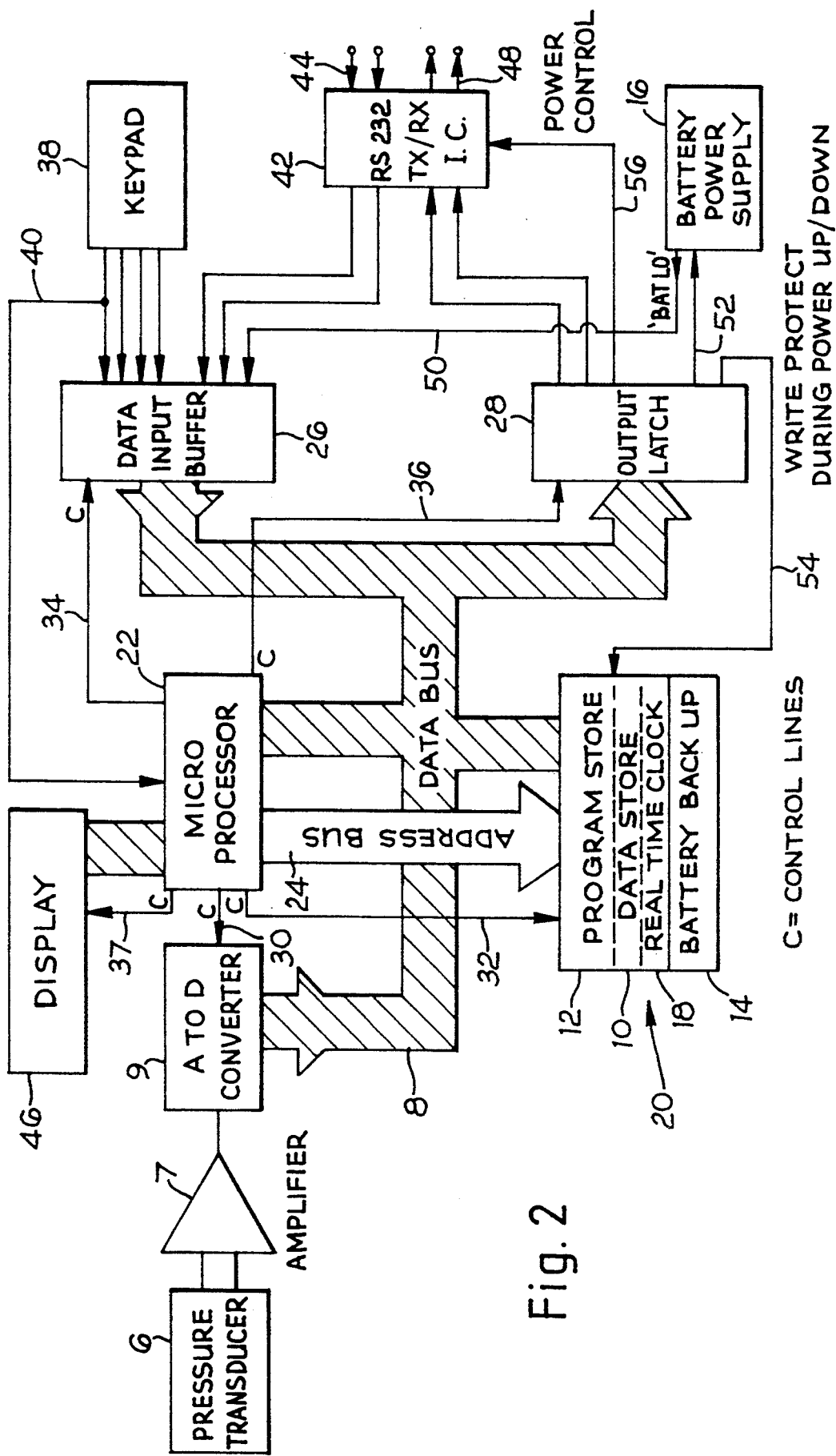
FIG. 2 is a schematic block diagram of the data processing system used in the apparatus of the present invention.

Referring now to FIG. 2, the pressure signals sensed are processed and stored by data processing means located within the casing 1. The signals of air pressure sensed by the transducer 6 are passed to an amplifier 7 and the amplified signal is received by an A-D converter 9. A data bus 8 carries the digitised signal from the converter to a data store 10. The data store 10 and a program store 12 for the operating program of the apparatus may be in the form of separate RAM and EPROM chips respectively. In the present example, however, a single RAM is used with a write-protected portion employed to hold the operating program. Means are provided to hold the stored data for prolonged periods between successive groups of readings and preferably this function is fulfilled by a back-up battery 14 separate from a main battery power source 16 for the apparatus. In the present example, data store 10, the program store 12, and backup battery 14, and also a real-time clock 18 controlling the operation of the program, are integrated as a unit 20 in a single proprietary chip (MK48T08B "Time Keeper" RAM from SGS Thompson Microelectronics).

Central processor 22 is also connected to the store and clock unit 20 through the data bus 8 and can address the program store through an address bus 24. The data bus 8 also provides an input channel from a data input buffer 26 and an output channel to an output latch 28. Control lines 30,32,34,36 extend from the processor 22 to the A-D converter 9, the store and clock unit 20, the input buffer 26 and the output latch 28. The internal structure of the microprocessor 22 will be further described with reference to FIG. 3.

Data can be input manually by a keypad 38 through the buffer 26 to the data store 10. Line 40 indicates a connection direct from the keypad 38 to the processor 22 that actuates the resetting of the apparatus, including the switching on of the supply from the main battery 16, in preparation for a set of readings.

A communication port 42 has output terminals 48 which can be employed to read data accumulated in the store onto a peripheral device, e.g. to a printer (not shown) and it is also possible to process the outputted data to display it directly on the VDU of a computer in manipulative graphical form. It is also possible to read stored data on a display panel of the device itself.

The communication port 42 provides an input channel to input commands for clearing the data store. Other sequences which are not normally intended to be under the control of the subject can be operated by coded signals from the keypad 38 but if preferred it may be arranged for the communication port to form the input for any or all of the commands not intended to be used by the subject. It is also possible to use the communication port 42 as an input to modify the operating program. Conveniently, the program store is hard-wired, but in that case, a portion of the program intended to be modifiable can be assigned to a part of the data store accessible via the communication port.

The power connections from the battery supply to the different units shown in the drawing are not illustrated. In the drawing there only appears a "battery low" signal line 50 to the data input buffer, by means of which a warning signal of the main battery state is generated by the processor and displayed to the user, and a control line 52 from the output latch 28 to the battery supply by means of which the main power supply is switched on and off for each period of use.

Since the clock of the data processing system operates in real-time it is arranged that the times of the stored readings are automatically recorded in the data store. The back-up battery 14 powers the stores 10,12 and clock 18 only when power is not supplied from the main battery and ensures that the clock time is maintained and the stored data continues to be held, even if the main battery supply should run low. In order to ensure that a disturbance at the moment of change-over to or from the back-up supply does not affect the stores, a write-protect signal is input to the unit 20 through line 54 from the output latch 28 during power up or down.

Figure 3:
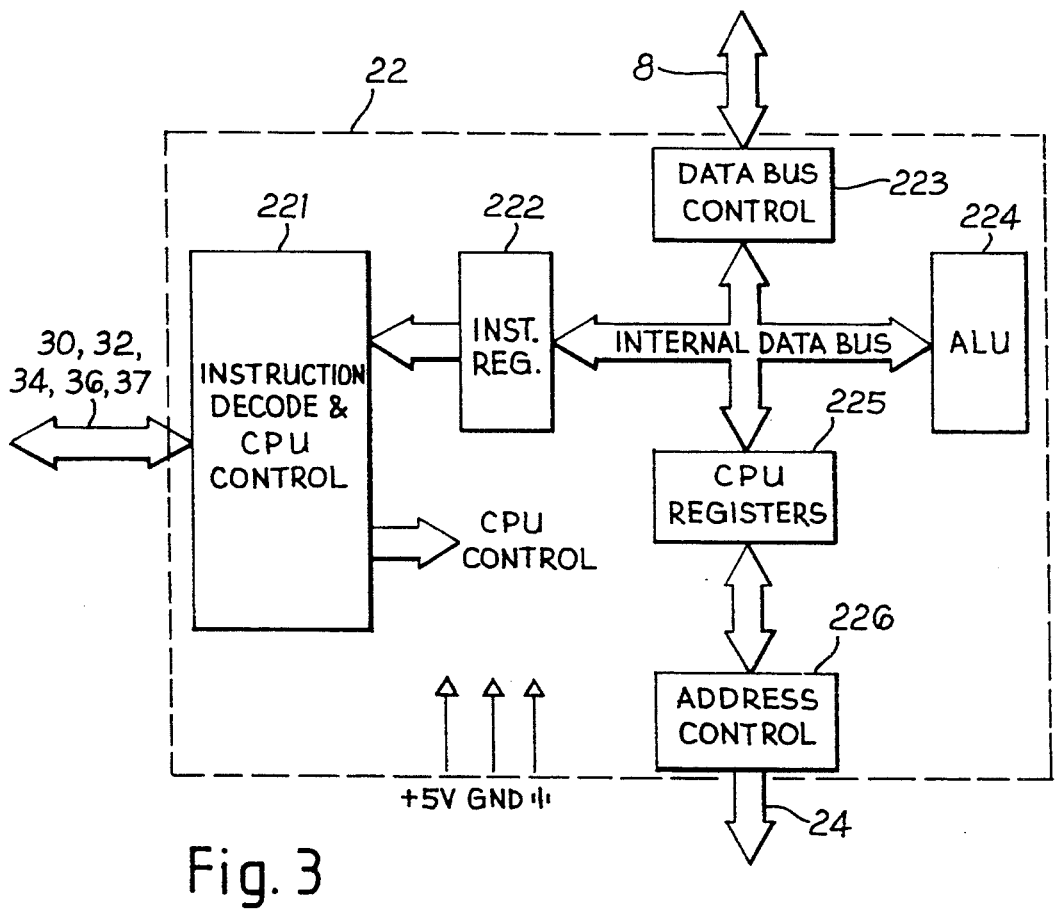
FIG. 3 is a block diagram showing the structure of the microprocessor 22 in FIG. 2.

FIG. 3 shows the internal structure of the microprocessor 22. An arithmetic and logical unit (ALU) 224 undertakes all the calculation and logical operations. Data needed by the ALU 224 is read in and sent out via the data bus control unit 223, the CPU registers 225 and the address control unit 226. Operational instructions are sent out via the instruction registers 222 and the instruction decode and CPU control unit 221.

In use, the subject will be provided with the apparatus with the program already loaded into the store. When required, he presses the keypad reset button to switch on the main power supply of the system. Using the keypad at the time of taking a set of readings, the subject can input information to be recorded in the data store in association with those readings, e.g. that he has used an inhaler or that he has taken exercise or medication. However, the inputs of the subject, in addition to the pressure transducer signals, are confined to such few limited information inputs that are available using the keypad.

A test sequence begins with the subject pressing a reset button on the keypad 38 which powers the data processing system from the main battery. The operating program actuates the ALU 224 in the microprocessor 22 to make a comparison of the peak pressure readings during a series of tests taking place within a set test period, e.g. 5 minutes, and to record in the data store the best two or three results during that period together with the time each such result was recorded. The apparatus can employ the visual display panel 46, which is under the control of the microprocessor 22 via the control line 37, to show the peak flow results for the information of the subject. Means may be provided to switch off the main battery at the end of the pre-set period for the series of tests and the stores and clock are powered by the back-up battery, as described. An interlock may also be provided to ensure that the power is not switched on again until the time approaches for the next set of readings.

The series of tests are repeated at the required intervals and the selected peak values and their times are added to the information in the data store. The store and clock unit 20 can also be provided with data indicating a series of preset test times for the subject. At the appropriate times a command is outputted to the microprocessor to actuate a reminder to the subject, e.g. a visual reminder on the display 46. In due course the subject's medical adviser can access the stored data of the appropriate peak pressure values related to specific test times through the communication port 42. The use of the back-up battery ensures that the stored data is retained until this is done, even if the subject should inadvertently have discharged the main power supply. As a further power conservation measure, the reset command through line 40 does not power the communication port 42 during the test readings. A separate read command button on the keypad 38 is used to actuate a signal on line 56 from the output latch which powers the port 42 when the data is to be accessed.

I claim:

1. An apparatus for measuring lung function of a subject, comprising:
   air passage means for receiving an exhalation of the subject;
   pressure sensing means for producing signals of the pressure in said air passage means during said exhalation;
   means for processing said signals to derive a peak value of the signal;
   means for comparing a plurality of peak values from the respective signals from a succession of exhalations within a predetermined time period;
   means responsive to said means for comparing for selecting a plurality of the highest peak values from the compared plurality of peak values;
   means for storing said selected peak values; and
   means for reading said stored peak values from said storing means.

2. An apparatus of claim 1, further comprising means for inputting into said storing means data auxiliary to the measurement.

3. An apparatus according to claim 2, wherein said inputting means comprises a keypad.

4. An apparatus according to claim 2, wherein the storing means comprises a program store and said inputting means is connected to said programming store for inputting commands for selecting changing data stored in said program store.

5. An apparatus according to claim 1, further comprising a dedicated power source connected to said storing means for holding therein data collected from a plurality of time periods.

6. An apparatus according to claim 1, further comprising a main power source for operation of the apparatus and a second battery power source connected to said storing means for holding data therein.

7. An apparatus according to claim 1, wherein said storing means comprises means for storing information relating to the time when a measurement is made.

8. An apparatus according to claim 1, further comprising means for indicating the start of a predetermined time at which a measurement is due to be made.

9. An apparatus according to claim 9, further comprising a readout means having a pointer and an associated scale; and a separate display panel connected to said processing means for displaying peak flow results and reminder information.

10. An apparatus according to claim 1, further comprising a casing in which said air passage means, said pressure sensing means, said processing means, said comparing means, said selecting means, said storing means and said reading means are disposed.

* * * * *